United States Patent [19]

Kanno et al.

[11] Patent Number: 5,288,517
[45] Date of Patent: Feb. 22, 1994

[54] METHOD OF FORMING PLANAR MEMBRANE

[75] Inventors: Tsunehiro Kanno, Isehara; Kinya Kato, Yokohama; Harumi Iwashita, Atsugi; Junji Ohyama, Yamato; Nobuko Yamamoto, Isehara; Masanori Sakuranaga, Atsugi, all of Japan

[73] Assignee: Canon Kabushiki Kaisha, Tokyo, Japan

[21] Appl. No.: 835,025

[22] Filed: Feb. 18, 1992

Related U.S. Application Data

[63] Continuation of Ser. No. 402,080, Aug. 21, 1989, abandoned.

[30] Foreign Application Priority Data

Aug. 26, 1988 [JP] Japan .................. 63-211911

[51] Int. Cl.$^5$ .................. G01N 33/545; C07K 17/08; B05D 5/00
[52] U.S. Cl. .................. 427/244; 427/299; 427/387; 424/450; 436/829; 530/359; 435/174; 435/177; 264/215; 264/212; 264/299
[58] Field of Search .................. 424/450; 436/829; 530/359; 427/244, 299, 387; 435/174, 177

[56] References Cited

PUBLICATIONS

Ishiguro, T. "Preparation of Supported Membranes Containing Transmembrane Proteins." J. Biochem., vol. 95 (1984) pp. 581-583.
Weis et al. "Stimulation of Fluorescence in a Small Contact Region Between Rat Basophil Leukemiacens and Planar LIPID Membrane Target by Coherent Evanscent Radiation." The Journal of Biological Chemistry, vol. 257 (1982) pp. 6440-6445.
Horio and Yamashita, "Tanpakushitsu Kosono Kisojikkenho (Basic Experimental Methods for Proteins and Enzymes)," 1981, pp. 147-149, Nankodo Co.
SPOP Heterobifunctional Reagent, Sweden, 1978, pp. 1-12 (Pharmacia Fine Chemicals).
Deamer, D. W. and Uster, P.S. "Liposome Preparation: Methods and Mechanisms." in: Osto, M. J., Liposomes (New York and Basel, Marcel Dekker, Inc. 1983), pp. 31-32.
Gruner, S. M. "Materials Properties of Liposomal Bilayers." in: Ostro, M. J., Liposomes from Biophysics to Therapeutics (New York and Basel, Marcel Dekker, Inc. 1987), pp. 4-5.
The Condensed Chemical Dictionary, 8th ed. New York, van Nostrand Reinhold Company, 1971 pp. 641 and 380.
Stryer, L. Biochemistry, USA., W. H. Freeman and Company/New York, 1988, pp. 289-290.
Chemical Abstract Data Sheet of CA;109(25) 225157a. Dec. 1988.

Primary Examiner—Allen J. Robinson
Assistant Examiner—John D. Pak
Attorney, Agent, or Firm—Fitzpatrick, Cella, Harper & Scinto

[57] ABSTRACT

A method of forming a lipid planar membrane of a bilayer membrane composed of lipid and protein comprises the step of immersing a substrate, which has a long-chain hydrocarbon group at least on the surface of one side thereof, in a suspension of liposome or proteoliposome, respectively. The long-chain hydrocarbon group is introduced into the substrate by bonding a long-chain alkylsilane coupling agent or a long-chain alkyltitanate coupling agent.

6 Claims, 1 Drawing Sheet

METHOD OF FORMING PLANAR MEMBRANE

This application is a continuation of U.S. application Ser. No. 07/402,080 filed Aug. 21, 1989, now abandoned.

BACKGROUND OF THE INVENTION

1. Field of the Invention

The present invention relates to a method of forming a planar bilayer membrane with a desired size on a substrate in a liquid phase, using a membrane-forming substance such as lipid or protein, under mild conditions and according to simple procedures.

2. Related Background Art

It is well known that biomembrane is comprised of a lipid bilayer membrane as a basic structure, and fulfill a great variety of functions because of the various membrane proteins present in the membrane in a mixed state. If an artificial membrane can be reconstructed to mimick a biomembrane, it can be utilized for the filtration or concentration of useful substances by controlling, for example, the permeability to substances. It can also be used for the adsorption and combination of a trace biotic substances by utilizing the affinity for the biotic substances. For example, enzyme or antibody sensors are developed which are capable of detecting substances by retaining enzymes or antibodies in the membrane and by measuring the membrane potential or change in membrane resistance occuring when they have attached to a specific substrate or antigen.

To carry out development of such functional membranes, required first of all technique is required for constructing a stable planar bilayer membrane of lipid. It is further preferred that protein can be introduced into the membrane under mild conditions. Hitherto known methods of preparing a planar membrane include the black membrane process and the Langmuir-Blodgett process (LB process).

The black membrane process utilized the phenomenon that, when a thin sheet made of plastics or the like in which minute holes of about 100 µm in diameter are made is immersed in an aqueous solution and a lipid dissolved in an organic solvent is applied on the minute holes, the solvent moves over the peripheries of the minute holes, so that a lipid bilayer membrane is formed at the central area.

The LB process is a process by which a monolayer, membrane or a built-up membrane thereof is formed by utilizing the phenomenon that, in molecules having a hydrophilic part and a hydrophobic part therein, or molecules having the parts that show a remarkable difference in the hydrophilic characteristics from each other the molecules form a monolayer with hydrophilic groups facing down on a water surface. These membranes are usually prepared using a Langmuir's water tank. This water tank is provided with a partition plate so that a molecular layer dispersed on the gas-liquid interface may not loosely disperse on the aqueous phase. Thus the dispersing area of the molecular layer spread can be restricted and hence the assembled state of the molecular layer can be restricted, and a surface pressure is obtained depending on the assembled state. The partition plate is moved so that the dispersing area may be reduced, thereby gradually increasing the surface pressure, and thus a surface pressure of the molecular layer can be set. Then, while maintaining the surface pressure, a clean substrate is gently moved upward and downward in the vertical direction or the substrate is horizontally laid on the molecular surface, so that the molecules can adhere to and be transferred on the substrate.

The membrane-forming substances such as protein and lipid are not necessarily stable under physical and chemical conditions in the conventional procedures for preparing planar membranes. The protein exhibits its function only when the polypeptide chain keeps a specific higher order structure, and tends to be denatured or inactivated as a result of the destruction of the higher order structure by interfacial tension, organic solvents or the like. The lipid also tends to undergo oxidation in the presence of oxygen.

In the black membrane process, in which an organic solvent is used in the procedure for preparing a membrane, it is commonly difficult to simultaneously introduce protein into the membrane. The organic solvent also inevitably remains in the membrane produced, and hence there is the difficulty of inactivation even when the protein is introduced according to, for example, proteoliposome fusion after the preparation of a membrane.

In the LB process, the membrane-forming substance must be previously dispersed as a monolayer membrane on the gas-liquid interface, so that the protein may sometimes be denatured by interfacial tension. There is also a possibility of the oxidation of lipid because of its contact with a gaseous phase.

Thus, the conventional methods of preparing the planar membrane, which have taken no account of the physical and chemical stability of molecules, have sometimes caused defects in the membrane particularly when protein or lipid originating from organisms is used, resulting in no exhibition of the expected functions. It is therefore sought to prepare the membrane under milder conditions.

The conventional methods of preparing the planar membrane further have the following disadvantages. In the black membrane process, the area and shape of the membrane that can be prepared are so extremely limited that it is impossible to prepare a membrane with a diameter of more than 1 mm. In preparing the membrane, a skilled operation is also required. Thus, they are not suitable for their industrial application.

The LB process is actually subject to various limitations based on, e.g., the shape of apparatus, in regard to the area and shape of the membrane, but is free from any limitations in principles. As previously mentioned, however, in the LB process the building-up of membranes in the molecular level is carried out by mechanical action, and hence delicate precision is required in controlling the surface pressure and moving the substrate. Moreover, because of use of the monolayer membrane dispersed on the gas-liquid interface, even a slight vibration of the water surface and inclusion of a trace of dust floating in the air may give defects to the membrane. Hence, in order to obtain an LB membrane with good quality, an investment must be made for the installation of an anti-vibration apparatus, a clean room, and so forth.

SUMMARY OF THE INVENTION

An object of the present invention is to overcome the above disadvantages involved in the conventional preparation methods for planar membranes and to form a bilayer membrane with a desired size, on a substrate in a liquid phase under such mild conditions that may not cause any denaturation or inactivation of the membrane-forming substance such as protein or lipid, following simple steps.

In summary, the present invention provides a method of forming a lipid bilayer planar membrane, comprising the step of immersing a substrate having on the surface of at least one side thereof a long-chain hydrocarbon group, in a suspension of liposome.

The present invention also provides a method of forming a bilayer membrane composed of lipid and protein, comprising the step of immersing a substrate having on the surface of at least one side thereof a long-chain hydrocarbon group, in a suspension of proteoliposome.

DESCRIPTION OF THE PREFERRED EMBODIMENT

The present invention is basically characterized by utilizing the phenomenon that liposome or proteoliposome is spontaneously cleaved in a liquid phase, on a substrate having a long-chain alkyl group on its surface, and is dispersed thereon to form a planar membrane.

More specifically, although it has been hitherto known that the liposome or proteoliposome is cleaved at the gas-liquid interface and dispersed to form a monolayer membrane, the present inventors have found that the liposome or proteoliposome is also cleaved at the interface between a liquid phase and a molecular layer on which the long-chain alkyl groups are arranged and dispersed as a monolayer membrane, and thus accomplished the present invention.

Figure 1:
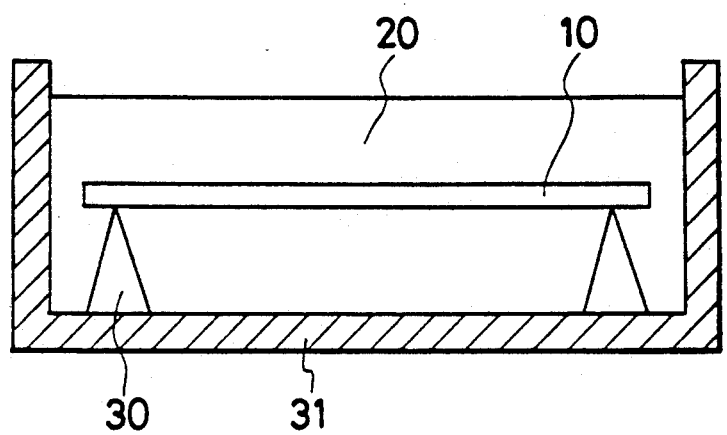
FIG. 1 schematically illustrates a basic constitution of the present invention.
Figure 2:
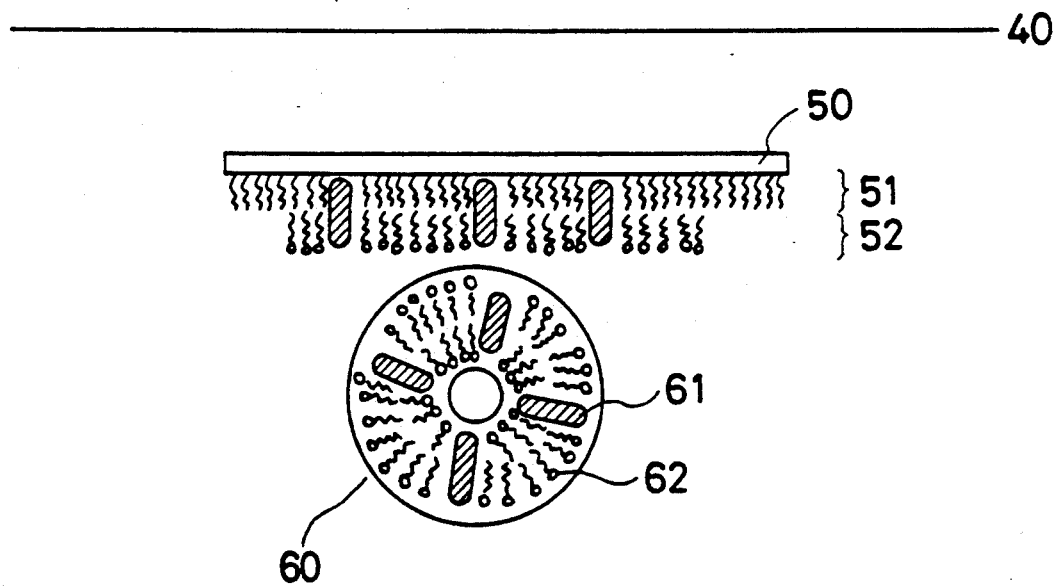
FIG. 2 schematically represents the procedure of the formation of a planar membrane.

FIGS. 1 and 2 schematically illustrate the constitution of the present invention. In FIGS. 1 and 2, the numerals 10 and 50 each denotes a substrate; 20, a liposome or proteoliposome suspension; 30, a substrate supporting member; 31, a dispersing tank; 40, the water surface; 51, a molecular layer of long-chain hydrocarbon groups; 52, part at which a planar membrane has been formed as a result of cleavage of liposome or proteoliposome; 60, liposome or proteoliposome (proteoliposome in the drawing); 61, a protein molecule; and 62, a lipid molecule. As illustrated in FIG. 1, a substrate to which long-chain hydrocarbon groups have been bonded is immersed in a liposome or proteoliposome suspension. FIG. 2 shows that the liposome or proteoliposome is cleaved on a hydrophobic surface to produce a planar membrane.

Since the step of preparing the membrane is carried out in a liquid phase, it is possible to set such conditions that may not result in loss of physiological activities of the membrane-forming substance such as protein or lipid. Since also the liposome or proteoliposome is spontaneously dispersed to form a planar membrane, the operation of, e.g., making precise movement of the substrate as in the conventional LB process is not required, thereby, making very the steps and apparatus very simple. In addition, there are no limitations on the area of the membrane from the standpoints of both the principle and practice, and hence a planar membrane with a large area can be obtained with simplicity.

Now, in the present invention, the planar membrane is dispersed on a substrate. As will be readily conjectured, the substrate may not necessarily be in the form of "true" plane, and there can be utilized those having a round surface or uneven surface. The substrate may be of any material so long as the hydrocarbon group can be imparted thereto, and there can be used, for example, glass, metals, ceramics, and resins. The substrate may not necessarily have a smooth surface, and there can be used, for example, porous glass, cellulose films, and colagen films. There can be further used those substrates which have been surface-treated with various fillers. As will be apparent from the constitution of the present invention, a planar membrane can be formed on the surface of the substrate immersed in the liquid phase, so long as a molecular layer comprising a hydrocarbon group is formed thereon. Hence, the planar membrane can be formed on both sides by imparting the hydrocarbon group to both sides of the substrate.

Methods of forming the monolayer in the present invention, comprised of the long-chain hydrocarbon group which is previously placed on the substrate, may include a method in which a long-chain alkyl coupling reagent is bonded to the substrate or a method in which a polar group of a lipid having a long-chain hydrophobic group is bonded to the substrate. The former is a simple method, in which a silane coupling agent may include an alkyltrichlorosilane:

or an alkyltrimethoxysilane:

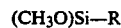

In particular, stearyltrichlorosilane is commercially available, and can be treated with simplicity. For the adhesion to resins or inorganic fillers, also preferred are alkyl titanates, as exemplified by:

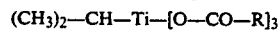

or

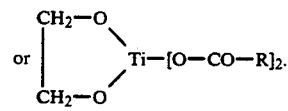

The method in which a polar group of a lipid is bonded to the substrate to introduce the long-chain hydrocarbon group into the substrate has somewhat complicated steps, but makes it easy to introduce the hydrocarbon group containing an unsaturated bond or enables formation of a gap between the hydrocarbon group and substrate, so that this method is particularly advantageous when using a protein which is large in the part exposed outside the bilayer membrane.

In the present invention, a liposome or proteoliposome suspension must be prepared in the first place. In preparing it, known amphiphatic compounds capable of constituting a monolayer membrane or multilayer membrane can be utilized as materials for the lipid. The lipid molecule having the ability of forming these membranes is constituted of a long-chain alkyl group having 8 or more carbon atoms and a hydrophilic group. The hydrophilic group may be any of cations as exemplified by:

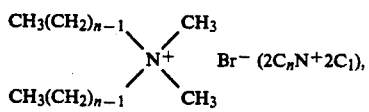

anions as exemplified by:

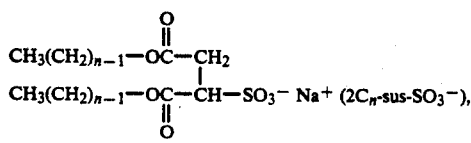

nonions as exemplified by:

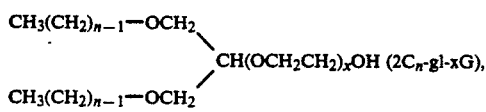

and ampho-ions as exemplified by:

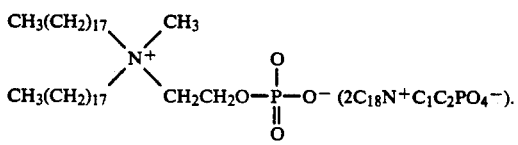

Of these materials for lipids, there may be used glycerophospholipids such as phosphatidylcholine (lecithin), phosphatidylethanolamine, and diphosphatidylglycerol; sphingophospholipids such as sphingomyelin, and ceramide ciliatin; sphingoglycolipids such as cerebroside, sulfatide, and ceramide oligohexocide; and glyceloglycolipids such as glycosyldiacyl glycerol containing a carbohydrate as a hydrophilic group. The materials for lipids referred to in the present invention are not limited to the above examples, and there are no particular limitations so long as they are capable of forming a bilayer membrane vesicle.

In the present invention, the liposome may be prepared by the methods usually used, without any particular expedients. For example, there can be used a method in which a lipid is solubilized using a detergent to prepare a mixture solution and the detergent is slowly removed from the solution according to dialysis (dialysis method); a method in which a lipid is added in an aqueous solution and suspended therein at a suitable temperature, and the suspension is applied with a mechanical vibration using a Vortex mixer or the like, followed by rapid cooling and gradual thrawing of the resulting suspension (freeze-thraw method); a method in which the suspension is subjected to sonication treatment (sonication method); a method in which an organic solvent solution of a lipid is mixed with water, followed by removal of the organic solvent (reverse phase evaporation method); and a method in which an alternating current electric field is applied to a vesicle suspension prepared (fusion method). These methods can also be used in combination, or other modified methods can also be used.

The proteoliposome may also be prepared by the methods usually used, similar to the methods of forming the liposome, without any particular expedients. For example, a detergent removal method such as the dialysis method or a hydrophobic bead treatment method, the freeze-thraw method, the reverse phase evaporation method, and the membrane fusion method are used for convenience. These methods can also be used in combination, or other modified methods can also be used.

So-called microsome fractions, obtained by crushing and centrifuging organism tissues such as cells and organelles, can also be used in the present invention in place of the proteoliposome. For example, liver microsome vesicles or muscle endoplasmic recticulum vesicles may be used.

The suspension of liposome or proteoliposome, prepared by the above methods, may be put in the spreading tank as shown in the drawing and the substrate to which the hydrocarbon groups have been bonded may be immersed therein. The present invention is thus accomplished.

As an example showing a basic constitution of the present invention, a method of spreading the bilayer lipid membrane on the planar substrate will be described below by giving an example.

There are no particular limitations on the substrate so long as the alkyl groups can be imparted to its surface. A glass sheet will be used here as an example. Silanol groups (—SiOH) are present on the surface of glass, and the use thereof can achieve direct alkylation of the substrate, employing an alkylsilane coupling agent having a methoxy group (—OCH$_3$), an ethoxy group (—OC$_2$H$_5$) or a halogen group (—X). A manner of alkylation of a glass surface with use of octadecyltrichlorosilane is published together with a step of pretreatment of the glass surface [see, for example, T. Ishiguro & M. Nakanishi, J. Biochem. 95, pp. 581–583 (1984)]. This can be applied to other silane coupling agents. There are no limitations on the length of the alkyl group and the degree of unsaturation. In practice, however, the types of commercially available silane coupling agents are relatively limited. In particular, those having an unsaturated bond are available with difficulty. On the other hand, as phospholipids, those with various lengths and degrees of unsaturation are available including natural ones and synthetic ones. Hence, it is advantageous if polar groups of a phospholipid can be bonded to the substrate. For this purpose, it is possible to use phopholipids having an amino group, phosphatidylethanolamine (PE), and phosphatidylserine (PS). Methods of combining the amino group to a solid phase having a plurality of hydroxyl groups exist in variety, among which a cyanogen bromide activation method, and a cross-linking method using a heterodivalent functional cross-linking reagent and SPDP (N-succinimidyl-3-(2-pyridylthio)propionate) can be advantageously used.

The cyanogen bromide activation method is a method in which a polysaccharide such as agarose, having a large number of hydroxyl groups, is treated with cyanogen bromide and converted into an active group so that it may be brought into covalent bond to the amino group of the compound such as protein. This can be used as it is, in the bonding between the glass surface having a silanol group and the phospholipid having an amino group. This method is described in detail in various experimental reports (for example, "TANPAKUSHITSU.KOSO NO KISOJIKKENHO (Basic Experimental Methods for Proteins and Enzymes)", edited by Horio and Yamashita, Nankodo Co., pp. 147–149, 1981), which was applicable without any particular modification.

The cross-linking method using SPDP is also a method in which SPDP is bonded to the amino group of phospholipid and converted into a thiol group (—SH), γ-mercaptopropyltrimethoxysilane is further bonded to a solid phase to make the surface similarly comprised of a thiol group, and both are reacted to form a disulfide bond. SPDP is first bonded to phospholipid. The reaction conditions are detailed in a pamphlet of Pharmacia Fine Chemicals, Inc., "SPDP, Heterobifunctional Reagent". In the reaction, however, both the phospholipid and SPDP are dissolved in ethanol in place of an aqueous solution, so that the reaction is carried out in ethanol. To separate an end product, i.e., a phospholipid-SPDP complex, from the reaction mixture, column chromatography is carried out in place of gel filtration, using a silica gel column and using chloroform-methanol as a developing solvent. The γ-mercaptopropyltrimethoxysilane can be bonded to the glass substrate under entirely the same conditions as in other silane coupling agents. In this way, the glass substrate to which a thiol is introduced is immersed in an ethanol solution of the phospholipid-SPDP complex. As a result, the phospholipid is fixed on the substrate through the disulfide bond.

In the above, the method of imparting hydrocarbon groups to the surface has been described assuming the glass as the substrate. However, substantially the same method can be applied so long as it is made of the material having hydroxyl groups on its surface. For example, the surface of a metal has usually been oxidized and the hydroxyl groups are produced in the presence of water. Gels of cellulose, agarose, etc. can also be used in the same manner. A polyacrylamide gel, having an amino group as a functional group, can also bring about the introduction of a thiol group when the SPDP is used as the cross-linking reagent, so that the hydrocarbon groups can be imparted using the phospholipid-SPDP complex.

Making the substrate hydrophobic has been almost described in the above. Regarding another remaining factor, for preparing the liposome or proteoliposome suspension, many of conventionally available preparation methods can be utilized as previously described. Regarding the respective preparation methods, a number of experimental reports set out details (for example, "MAKUSHISHITSU TO KESSHO RIPOTAN-PAKUSHITSU (Membrane Lipid and Plasma Lipoprotein) (The 3rd Volume)", chapters 24, 25, The Biochemical Experiment Course, Continued, Vol. 3, edited by Japan Biochemical Society). Accordingly, no detailed description will be made here in regard to the respective preparation methods.

EXAMPLES

The present invention will be described below in detail by giving specific Examples.

Example 1

Cover glass (10 mm × 10 mm in approximation) is washed with a heated 5% Extran (Merck & Co., Inc.) solution, and then treated with a water-bath type ultrasonic washer for 30 minutes. After washing with running water for 30 minutes, the cover glass thus treated is dried in an oven of 110° to 150° C. The dried cover glass is immersed in a solution of 2 ml of octadecyltrichlorosilane, 140 ml of n-hexadecane, 30 ml of carbon tetrachloride and 20 ml of chloroform, followed by stirring at room temperature for 2 hours. The cover glass is taken out, washed three times with chloroform and once with ethanol, and thereafter dried in an oven of 110° C.

The above operation completes the alkylation of the surface of the cover glass.

A chloroform solution of egg yolk lecithin corresponding to 150 mg of lipid weight is put in a 30 ml round-bottom flask, and, after the solvent is evaporated using a rotary evaporator, put in a desiccator to completely remove the solvent with use of a vacuum pump. An aqueous solution of, for example, 0.1M KCl and 10 mM Tris-HCl (pH 7.0) is added in an amount of 10 ml, and the resulting mixture is treated with a Vortex mixer for 30 seconds to 1 minute to make lipid thin membranes dispersed, followed by sonication treatment using a probe type sonication oscillator for 30 minutes. As a result, there is obtained a suspension of unilameller liposome of not more than 100 nm in diameter. This is frozen with liquid nitrogen or dry-ice/acetone, and is then thrawed at room temperature, followed by treatment with a water-bath type sonicator to obtain a suspension of unilameller liposome of not more than several 100 nm in diameter.

The liposome suspension is poured into a spreading tank having the structure as illustrated in FIG. 1, and the alkylated cover glass is immersed in the liposome suspension. The cleavage of liposome on the alkylated substrate and the formation of the bilayer membrane are effected at a rate that becomes higher with an increase in the concentration of lipid, and completed in about 30 minutes under conditions of a lipid concentration of 20 mg/ml.

Example 2

Here is described a method in which a planar bilayer membrane containing protein is formed using proteoliposome comprised of protein introduced into its membrane, in place of the liposome comprised only of lipid.

A porous glass (for example, MPG-D, produced by Asahi Glass Co., Ltd.; pore size: 40 Å, disc diameter: 10 mm) is used as the substrate. The substrate is washed with chloroform, and then dried in an oven. The dried substrate is immersed in a 2% chloroform solution of γ-mercaptopropyltrimethoxysilane (SH6002, available from Shin-Etsu Chemical Co., Ltd.), followed by stirring for 1 hour. The substrate is taken out, washed with chloroform, and thereafter dried in an oven of 100° C. for 10 minutes. The surface of the porous glass substrate is thiolated as a result of the above operation.

On the other hand, an ethanol solution of phosphatidylethanolamine (PE) (10 mg/ml) and an ethanol solution of SPDP (N-succinimidyl-3-(2-pyridylthio)propionate; available from Pharmacia Fine Chemicals, Inc.) are mixed, and the mixture is left to stand at room temperature for 1 hour to allow them to react. After the reaction is completed, unreacted PE and SPDP are removed by column chromatography carried out using a column of silica gel, and chloroform-methanol as a developing solvent, to obtain a PE-SPDP complex.

The PE-SPDP complex is formed into an ethanol solution thereof, and the thiolated porous glass substrate is immersed in the solution. As a result, disulfide bonds are formed and thus PE is fixed on the substrate. The substrate on which the PE has been fixed is washed with ethanol, followed by suction for 1 hour using a vacuum pump in a desiccator to completely remove ethanol.

As an example of the protein introduced into the planar membrane, bacteriorhodopsin is used. A purple membrane is extracted from halophilic archaebacterium *Halobacterium halobium* according to the method of P. Oesterhelt and W. Stoeckenius [Method. Enzymol., 31, 667-678 (1974)]. The purple membrane is further subjected to delipidation using the method of K. S. Huang et al [Proc. Natl. Acad. Sci. U.S.A., 77, 323 (1980)] to prepare bacteriorhodopsin.

A chloroform solution of soybean phospholipid (asolectin) corresponding to 150 mg of lipid weight is put in a 30 ml round-bottom type flask, and, after the solvent is evaporated using a rotary evaporator, put in a desiccator to completely remove the solvent with use of a vacuum pump. 10 ml of 0.1M KCl is added, and the resulting mixture is treated with a Vortex mixer for 30 seconds, followed by treatment using a probe type ultrasonic oscillator sonicator for 30 minutes. A required amount of bacteriorhodopsin is added to the resulting mixture, which is then freezed with liquid nitrogen or dry-ice/acetone, and is then thrawed at room temperature, followed by treatment with a water-bath type sonicator. This cycle is repeated 6 times. A unilamellar proteoliposome comprised of bacteriorhodopsin incorporated into the membrane is obtained as a result of the above operations.

The bacteriorhodopsin-proteoliposome suspension is introduced into a spreading tank, and the porous glass substrate on which PE has been fixed is immersed therein. Like the case of liposome, the cleavage on the proteoliposome substrate and the formation of the bilayer membrane composed of lipid and protein are effected at a rate that becomes higher with an increase in the concentration of proteoliposome, and completed in about 30 minutes under conditions of a lipid concentration of 20 mg/ml.

Examination on the spectral characteristics of the substrate on which the planar membrane has been formed according to the above operations was made to reveal that there are shown similar characteristics to those of the purple membrane, and that hydrogen ions migrate through the porous glass and the pH of the solution changes as a result of irradiation with light having a sufficient intensity at around 560 nm, thus having confirmed that the bacteriorhodopsin has been incorporated into the planar membrane formed and also the physiological functions are maintained.

As having been described above, the method of forming the planar membrane according to the present invention is finished with the step in a liquid phase, and hence not only has the advantage that the contamination by dust in a gaseous phase or the influence by vibration of water surface can be eliminated when compared with the conventional membrane formation method utilizing the cleavage at the gas-liquid interface, but also provides a mild membrane preparation method which is free from the loss of physiological activities of the membraneforming substance such as protein and lipid. Since the steps are simple and no particular apparatus is required, a planar bilayer membrane composed of lipid and planar which is of large area, stable, and of good quality can be obtained in a low cost and with simplicity.

We claim:

1. A method of forming a lipid planar bilayer membrane, comprising the steps of selecting a liquid phase comprising a suspension of liposome; and immersing a substrate having on the surface of at least one side thereof a molecular layer of long-chain hydrocarbon groups in said liquid phase, whereby said liposome is cleaved, on the surface of said molecular layer in said liquid phase and is disposed as a monolayer on said molecular layer.

2. A method of forming a lipid planar bilayer membrane according to claim 1, wherein said substrate having said hydrocarbon groups is constituted by bonding to the substrate an alkylsilane coupling agent or an alkyltitanate coupling agent.

3. A method of forming a lipid planar bilayer membrane according to claim 1, wherein said substrate having said hydrocarbon groups is constituted by bonding to the substrate a polar group of a lipid having a fatty acid chain.

4. A method of forming a bilayer membrane composed of lipid and protein, comprising the steps of immersing a substrate having on the surface of at least one side thereof a molecular layer of long-chain hydrocarbon groups; and immersing said substrate in a liquid phase comprising a suspension of proteoliposome whereby said proteoliposome is cleaved, on the surface of said molecular layer in said liquid phase and is disposed as a monolayer on said molecular layer.

5. A method of forming a planar bilayer membrane composed of lipid and protein according to claim 4, wherein said substrate having said long-chain hydrocarbon groups is constituted by bonding to the substrate an alkylsilane coupling agent or an alkyltitanate coupling agent.

6. A method of forming a planar bilayer membrane composed of lipid and protein according to claim 4, wherein said substrate having said long-chain hydrocarbon groups is constituted by bonding to the substrate a polar group of a lipid having a fatty acid chain.

* * * * *

UNITED STATES PATENT AND TRADEMARK OFFICE
CERTIFICATE OF CORRECTION

PATENT NO. : 5,288,517
DATED : February 22, 1994
INVENTOR(S) : TSUNEHIRO KANNO, ET AL.

Page 1 of 2

It is certified that error appears in the above-identified patent and that said Letters Patent is hereby corrected as shown below:

COLUMN 1

Line 17, "fulfill" should read --fulfills--.
Line 21, "mick" should read --mic--.
Line 24, "trace" should read --trace of--.
Line 33, "required" (first occurrence) should be deleted and "all" should read --all,--.

COLUMN 3

Line 40, "denotes" should read --denote--.
Line 62, "very" should be deleted.

COLUMN 5

Line 53, "thrawing" should read --thawing--.
Line 54, "(freeze-thraw" should read --(freeze-thaw--.

COLUMN 6

Line 1, "freeze-thraw" should read --freeze-thaw--.

COLUMN 9

Line 18, "freezed" should read --frozen--.
Line 19, "thrawed" should read --thawed--.

UNITED STATES PATENT AND TRADEMARK OFFICE
CERTIFICATE OF CORRECTION

PATENT NO. : 5,288,517
DATED : February 22, 1994
INVENTOR(S) : TSUNEHIRO KANNO, ET AL.

It is certified that error appears in the above-identified patent and that said Letters Patent is hereby corrected as shown below:

COLUMN 10

Line 4, "braneforming" should read --brane-forming--.

Signed and Sealed this

Twenty-second Day of November, 1994

Attest:

BRUCE LEHMAN

*Attesting Officer*          *Commissioner of Patents and Trademarks*